(12) United States Patent
Bertram et al.

(10) Patent No.: US 11,751,827 B2
(45) Date of Patent: Sep. 12, 2023

(54) METHOD AND SYSTEM FOR DETERMINING THE CONFIGURATION OF A MEDICAL IMAGING SYSTEM

(71) Applicant: Brainlab AG, Munich (DE)

(72) Inventors: Michael Bertram, Markt Schwaben (DE); Florian Glatz, Munich (DE); Georg Christian, Neufahrn (DE)

(73) Assignee: Brainlab AG, Munich (DE)

(*) Notice: Subject to any disclaimer, the term of this patent is extended or adjusted under 35 U.S.C. 154(b) by 419 days.

(21) Appl. No.: 17/269,704

(22) PCT Filed: Sep. 24, 2019

(86) PCT No.: PCT/EP2019/075752
§ 371 (c)(1),
(2) Date: Feb. 19, 2021

(87) PCT Pub. No.: WO2021/058094
PCT Pub. Date: Apr. 1, 2021

(65) Prior Publication Data
US 2021/0345979 A1 Nov. 11, 2021

(51) Int. Cl.
*A61B 6/12* (2006.01)
*A61B 6/00* (2006.01)

(52) U.S. Cl.
CPC ............ *A61B 6/487* (2013.01); *A61B 6/4452* (2013.01); *A61B 6/469* (2013.01)

(58) Field of Classification Search
CPC ... A61B 34/20; A61B 2090/376; A61B 34/25; A61B 2017/00053; A61B 6/584; A61B 8/0841; A61B 2090/0811; A61B 6/032; A61B 2090/3983; A61B 5/06; A61B 5/061; A61B 34/10; A61B 6/487; A61B 2034/2065; A61B 2090/364; A61B 5/7425; A61B 5/065; A61B 5/4887; A61B 2034/107; G06T 2207/10116; G06T 2207/10121; G06T 2210/41; G06T 7/70; G06T 7/74; G06T 7/80

See application file for complete search history.

(56) References Cited

U.S. PATENT DOCUMENTS

| | | | |
|---|---|---|---|
| 2002/0118793 | A1 | 8/2002 | Horbaschek |
| 2008/0089467 | A1 | 4/2008 | Lauritsch |
| 2009/0180594 | A1 | 7/2009 | Saladin |

(Continued)

OTHER PUBLICATIONS

International Search Report and Written Opinion for corresponding international application No. PCT/EP2019/075752, dated Jun. 26, 2020. 11 pages.

*Primary Examiner* — Don K Wong
(74) *Attorney, Agent, or Firm* — Tucker Ellis LLP (57) ABSTRACT

This document relates to determining the configuration of a medical imaging system, in particular a configuration which defines a desired viewing direction of the medical imaging system onto a patient. First, a fluoroscopic image of at least a part of a patient is captured using the medical imaging system and the target central beam is set in the fluoroscopic image. Then a target line in space is determined which, when projected into the fluoroscopic image, coincides with the set target central beam. Then the configuration of the medical imaging system is determined such that the central beam of the medical imaging system coincides with the target line in space.

16 Claims, 4 Drawing Sheets

(56) References Cited

U.S. PATENT DOCUMENTS

2012/0259204 A1\* 10/2012 Carrat .................... A61B 34/20
  600/414
2013/0003927 A1 1/2013 Tsujii \* cited by examiner

METHOD AND SYSTEM FOR DETERMINING THE CONFIGURATION OF A MEDICAL IMAGING SYSTEM

RELATED APPLICATION DATA

This application is a national phase application of international Application No. PCT/EP2019/075752, filed Sep. 24, 2019, the contents of which are incorporated herein by reference.

FIELD OF THE INVENTION

The present invention relates to a method for determining the configuration of a medical imaging system, a corresponding computer program, a program storage medium storing such a program and a computer for executing the program, as well as a medical system comprising the aforementioned computer.

TECHNICAL BACKGROUND

The medical imaging system typically comprises an x-ray source which emits a conical x-ray beam, which can optionally be shaped using a collimator. The medical imaging system further typically comprises a two-dimensional x-ray detector for detecting the x-ray beam after it has passed the patient. With such a medical imaging system, a two-dimensional fluoroscopic image can be captured. However, it is also possible that the medical imaging system comprises an x-ray source emitting a fan-shaped x-ray beam and a line x-ray detector corresponding to the fan-shaped x-ray beam. Such an imaging system captures a one-dimensional x-ray image, but a two-dimensional fluoroscopic image can be obtained by moving the medical imaging system relative to the patient and combining a plurality of one-dimensional x-ray images. The center of the x-ray beam is also referred to as the central beam of the medical imaging system.

The x-ray source and the x-ray detector are mounted on a gantry of the medical imaging system, wherein the x-ray source and the x-ray detector can be moved relative to the gantry or a part thereof. The x-ray source and the x-ray detector can be arranged to be moved together relative to the gantry (or a part thereof) or that they can be moved individually relative to the gantry (or a part thereof). The gantry can comprise a base and a moveable part, wherein the x-ray source and the x-ray detector are arranged on the moveable part. The moveable part can for example be tiltable relative to the base, for example about one or more axes. In one implementation, these axes are perpendicular to each other.

The medical imaging system further comprises at least an x-ray source collimator in front of the x-ray source for shaping the beam of the x-ray source. The medical imaging system can further comprise an x-ray detector collimator in front of the x-ray detector for spatially filtering the detected x-rays. The geometry of a collimator is adjustable, such that the shape and/or size of the x-ray beam or the structure of the spatial filtering can be modified. The geometry of the collimator is described by settings of the collimator. The settings might in particular describe the positions of elements within the collimator.

The x-ray beam emitted by the x-ray source has a central axis, which is referred to as the native central beam of the medical imaging system. The x-ray beam after shaping by the by the x-ray source collimator also has a central axis, which is referred to as the central beam (of the medical imaging system). It represents the center of an image captured using the medical imaging system. Depending on the settings of the collimator, the direction of the central beam can differ from the direction of the native central beam.

The configuration of the medical imaging system comprises the position of the x-ray source, the position of the x-ray detector and the settings of the x-ray source collimator. The positions of the x-ray source and the x-ray detector are defined in a reference system of the medical imaging system. If the base of the gantry is fixed, the reference system can be the reference system of the base. If the base of the gantry is movable, the reference system can be a global reference system, such as a reference system assigned to a room in which the medical imaging system is used. However, it can be any other suitable reference system, such as an earth-based reference system or the reference system of a medical navigation system.

In this document, a position is defined in up to three translational dimensions defining a location and/or up to three rotational dimensions defining an alignment in space.

The present invention can be used for improving a workflow e.g. in connection with a medical imaging system such as AIRO®, which is a product of Brainlab AG, or any other suitable imaging system.

Aspects of the present invention, examples and exemplary steps and their embodiments are disclosed in the following. Different exemplary features of the invention can be combined in accordance with the invention wherever technically expedient and feasible.

Exemplary Short Description of the Invention

In the following, a short description of the specific features of the present invention is given which shall not be understood to limit the invention only to the features or a combination of the features described in this section.

This document relates to determining the configuration of a medical imaging system, in particular a configuration which defines a desired viewing direction of the medical imaging system onto a patient. First, a fluoroscopic image of at least a part of a patient is captured using the medical imaging system and the target central beam is set in the fluoroscopic image. Then a target line in space is determined which, when projected into the fluoroscopic image, coincides with the set target central beam. Then the configuration of the medical imaging system is determined such that the central beam of the medical imaging system coincides with the target line in space.

General Description of the Invention

In this section, a description of the general features of the present invention is given for example by referring to possible embodiments of the invention.

In general, the invention reaches the aforementioned object by providing, in a first aspect, a method of determining a configuration of a medical imaging system comprising an x-ray source and an x-ray detector mounted on a gantry and an x-ray source collimator for shaping the beam of the x-ray source, the configuration of the medical imaging system comprising the position of the x-ray source, the position of the x-ray detector and the settings of the x-ray source collimator.

The first step of the method is capturing a fluoroscopic image of at least a part of a patient with a known configuration of the medical imaging system. The fluoroscopic image is captured by the medical imaging system. The configuration of the medical imaging system being known means that the viewing direction of the fluoroscopic image in the reference system of the medical imaging system is known.

The second step is setting a target central beam of medical imaging system in the fluoroscopic image. The target central beam defines the desired viewing direction of a subsequent image captured using the medical imaging system, wherein the configuration of the medical imaging system to be determined shall be used for capturing the subsequent image. The target central beam is a straight line.

The third step is determining a target line in space from the target central beam and the known configuration of the medical imaging system.

The fourth step is determining the configuration of the medical imaging system such that the central beam of the medical imaging system coincides with the target line in space. As outlined above, the configuration of the medical imaging system comprises the positions of the x-ray source and of the x-ray detector as well as the settings of the x-ray source collimator. For example, a model of the medical imaging system can be used for determining simulated central beams of the medical imaging system for different sets of a position of the x-ray source, a position of the x-ray detector and particular settings of the x-ray source collimator. For example, a brute force algorithm of a suitable optimization algorithm can be used to find a configuration for which the central beam the medical imaging system coincides with the target line in space.

In one embodiment, the target line in space lies in a target plane in space defined by the position of the target central beam set in the fluoroscopic image. Since the viewing direction of the fluoroscopic image in the reference system of the medical imaging system is known due to the known configuration of the medical imaging system when capturing the fluoroscopic image, the target central beam set in this step defines the target plane in the reference system of the medical imaging system. The target line in space lies in this plane.

Now that the target plane in which the target line in space lies is known, there are two parameters missing for unambiguously defining the target line: one rotational parameter defining the orientation of the target line in the plane and a translational parameter defining the location of the target line in the plane. Several approaches for determining those two parameters will be described below.

In one embodiment of determining the rotational parameter of the target line in space, the angle between the target line in space and a reference line, which is perpendicular to the image plane of the fluoroscopic image and lies in the projected plane, is within a predetermined angular range. In one example, the angular range is from 80 degrees to 100 degrees, for example 90 degrees.

This embodiment assumes that the desired central beam of the medical imaging system has a particular orientation relative to the viewing direction of the fluoroscopic image. This is the case, for example, if the viewing direction of the fluoroscopic image is a lateral direction of a patient and the direction of the central beam of the medical imaging system for capturing the subsequent image should basically be the anterior-posterior direction of the patient.

In an alternative embodiment, the method involves a step of determining a medical workflow to be carried out, for example by user input, determining the viewing direction of the fluoroscopic image from this workflow and the desired direction of the central beam of the medical imaging system in a subsequent step of the medical workflow in which another image of the patient is to be taken using the medical imaging system. The rotational parameter can then be calculated from this information.

In another alternative, a method involves receiving user input which defines the rotational parameter.

One embodiment of determining the translational parameter of the target line in space comprises the step of inputting a depth location of the target line in space in a direction perpendicular to the image plane of the fluoroscopic image. The depth location can for example be input by a user. The depth location of the target line in space for example defines a position in a direction perpendicular to the image plane of the fluoroscopic image and thus defines the translational parameter of the target line in space.

In an alternative embodiment, the translational parameter is determined from a medical workflow in an analog manner as described for the rotational parameter above.

In another alternative embodiment, the translational parameter is determined automatically from the size of the medical imaging system. For example, the translational parameter is set such that the target line in space crosses the central beam of the medical imaging system when the fluoroscopic image was captured in the middle between the x-ray source and the x-ray detector. This alternative is a suitable generic approach, for example if the patient is positioned in a central area of the medical imaging system.

If a proposal for the rotational parameter and/or the translational parameter is made automatically, the proposal is presented to a user and user input for confirming proposal and/or amending the proposal is received.

In one embodiment, the method further involves the step of selecting a region of the patient to be imaged in the fluoroscopic image and determining the settings of the x-ray source collimator according to the selected region. In this embodiment, the size and/or shape of the x-ray beam is selected such that the region to be imaged is radiographed by the x-ray beam. The required size and/or shape of the x-ray beam is defined by the size and the location of the region to be imaged and the geometric properties of the medical imaging system, in particular the distance between the x-ray source and the x-ray detector.

In one embodiment, the method further comprises the step of selecting a region of the patient to be imaged in the fluoroscopic image. In this embodiment, determining the configuration of the medical imaging system involves the step of determining whether the x-ray source collimator is adjustable such that the central beam of the medical imaging system coincides with the target line in space and an x-ray beam shaped by the x-ray source collimator covers the region to be imaged while maintaining the current positions of the x-ray source and the x-ray detector. In other words, it is determined whether the desired central beam can be obtained by adjustment of the collimator only or a movement of at least one of the x-ray source and the x-ray detector is necessary.

If the collimator is adjustable in this way, the method involves adjusting the settings of the x-ray source collimator such that the central beam of the medical imaging system coincides with the target line in space and an x-ray beam shaped by the x-ray source collimator covers the region to be imaged. If the x-ray source collimator is not adjustable in this way, the method involves adjusting the positions of the x-ray source at the x-ray detector such that the native central beam of the medical imaging system coincides with the target line in space and determining the settings of the x-ray source collimator such that an x-ray beam shaped by the x-ray source collimator covers the region to be imaged.

In this embodiment, a physical movement of the x-ray source and/or the x-ray detector is avoided if the desired central beam of the medical imaging system can be obtained by adjustment of the x-ray source collimator only. This avoids any inaccuracies which might occur when re-positioning the x-ray source and/or the x-ray detector.

In one implementation of this embodiment, determining whether the x-ray source collimator is adjustable such that the central beam of the medical imaging system coincides with the target line in space and an x-ray beam shaped by the x-ray source collimator covers the region to be imaged via maintaining the current positions of the x-ray source and the x-ray detector involves calculating a required beam shape for imaging the selected region to be imaged and using a model of the x-ray source and the x-ray source collimator to determine whether they can form an x-ray beam of the required beam shape.

In one embodiment, setting the target central beam of the medical imaging system in the fluoroscopic image involves the steps of automatically generating a proposed target central beam, overlaying the proposed target central beam over the fluoroscopic image, obtaining user input regarding the proposed target central beam and modifying the proposed target central beam or approving the proposed target central beam according to the user input.

Automatic generation of the proposed target central beam can for example be based on information about a medical workflow being performed. Information about the desired viewing direction of an image to be captured using the medical imaging system in a subsequent workflow step might be used to propose a target central beam.

The proposed target central beam can also be based on feature detection. A particular feature is identified in the fluoroscopic image and the target central beam is placed relative to the detected feature. One feature might be a part of a bone structure, such as an end plate of a vertebra. In this example, the target central beam is set to be parallel to the end plate of the vertebra. Another feature might be a tool shown in the fluoroscopic image, such as a screw attached to a bone. In this case, a proposal could be that the target central beam lies in the axis of the screw.

It shall be noted that using or applying the tool is not part of the claimed method. The method only involves utilizing the tool shown in the fluoroscopic image for making a proposal for the target central beam.

There are many other examples of features in the fluoroscopic image which can be used for making a proposal for the target central beam. Such features might involve pedicles, any other anatomical object or implant. The proposal might also be based on regions of risk which shall receive as little x-ray energy as possible. A proposal for the target central beam can be made such that those regions of risk are avoided.

An alternative to automatically generating a proposed target central beam is receiving manual user input, for example by drawing a line in the fluoroscopic image, for example using a mouse, a touch pad, a touch screen or any other suitable input device.

In one embodiment, determining the configuration of the medical imaging system such that the central beam of the medical imaging system coincides with the target line in space involves the steps of acquiring an automatic model of the medical imaging system including all degrees of freedom of the x-ray source and the x-ray detector relative to the gantry, determining target positions of the x-ray source and the x-ray detector in space from the target line in space and the settings of the x-ray source collimator and determining the position of the gantry in space and the positions of the x-ray source and the x-ray detector relative to the gantry from the target positions of the x-ray source and the x-ray detector in space and based on inverse kinematics using the kinematic model of the medical imaging system.

The settings of the x-ray source collimator used in the step of determining the target positions are for example based on the size of a region to be imaged as explained above. Depending on the settings of the x-ray source collimator, the direction of the central beam might differ from the direction of the native central beam of the medical imaging system and the target position of at least the x-ray source is determined such that the actual direction of the central beam, depending on the settings of the x-ray source collimator, coincides with the target line in space. The target position of the x-ray detector can also be determined based on those parameters, for example such that the central beam hits the center of the x-ray detector.

The target positions are defined in the reference system of the medical imaging system. Once the target positions are known, the required position of the gantry and the positions of the x-ray source and the x-ray detector relative to the gantry can be determined.

In one embodiment, the method further comprises the step of driving actuators of the medical imaging system such that the medical imaging system assumes the determined configuration. This means that the components of the medical imaging system are automatically positioned and/or adjusted for capturing a subsequent medical image from the desired viewing direction. The actuators are optionally part of the medical imaging system.

The present invention further relates to a program which, when running on a computer that is connected to a medical imaging system comprising an x-ray source and an x-ray detector mounted on a gantry and an x-ray source collimator for shaping the beam of the x-ray source, causes the computer to determine the configuration of the medical imaging system, comprising the position of the x-ray source, the position of the x-ray detector and the settings of the x-ray source collimator, by executing the steps of:

acquiring a fluoroscopic image of at least a part of a patient with a known configuration of the medical imaging system,
  setting a target central beam of the medical imaging system in the fluoroscopic image,
  determining a target line in space from the target central beam and the known configuration of the medical imaging system and
  determining the configuration of the medical imaging system such that the central beam of the medical imaging system coincides with the target line in space.

The program corresponds to the method described above, and therefore achieves the same technical effects, but relates to mere data processing aspects.

The present invention further relates to a computer on which the aforementioned program is stored and/or run.

The present invention further relates to a system comprising said computer and a medical imaging system comprising an x-ray source and an x-ray detector mounted on a gantry and an x-ray source collimator for shaping the beam of the x-ray source.

Still further, the present invention relates to a non-transitory computer readable storage medium on which said program is stored.

For example, the invention does not involve or in particular comprise or encompass an invasive step which would represent a substantial physical interference with the body requiring professional medical expertise to be carried out and entailing a substantial health risk even when carried out with the required professional care and expertise.

For example, the invention does not comprise a step of performing an incision. More particularly, the invention does not involve or in particular comprise or encompass any surgical or therapeutic activity. The invention is instead directed as applicable to preparation of an incision. For this preparation alone, no surgical or therapeutic activity and in particular no surgical or therapeutic step is necessitated or implied by carrying out the invention.

Use of the Device or System

The present invention also relates to the use of the device/system or any embodiment thereof for determining the configuration of a medical imaging system.

Definitions

In this section, definitions for specific terminology used in this disclosure are offered which also form part of the present disclosure.

Computer Implemented Method

The method in accordance with the invention is for example a computer implemented method for performing the method steps or instructing an entity to perform a method step as appropriate. For example, all the steps or merely some of the steps (i.e. less than the total number of steps) of the method in accordance with the invention can be executed by a computer (for example, at least one computer). An embodiment of the computer implemented method is a use of the computer for performing a data processing method. An embodiment of the computer implemented method is a method concerning the operation of the computer such that the computer is operated to perform one, more or all steps of the method.

The computer for example comprises at least one processor and for example at least one memory in order to (technically) process the data, for example electronically and/or optically. The processor being for example made of a substance or composition which is a semiconductor, for example at least partly n- and/or p-doped semiconductor, for example at least one of II-, III-, IV-, V-, VI-semiconductor material, for example (doped) silicon and/or gallium arsenide. The calculating or determining steps described are for example performed by a computer. Determining steps or calculating steps are for example steps of determining data within the framework of the technical method, for example within the framework of a program. A computer is for example any kind of data processing device, for example electronic data processing device. A computer can be a device which is generally thought of as such, for example desktop PCs, notebooks, netbooks, etc., but can also be any programmable apparatus, such as for example a mobile phone or an embedded processor. A computer can for example comprise a system (network) of "sub-computers", wherein each sub-computer represents a computer in its own right. The term "computer" includes a cloud computer, for example a cloud server. The term computer includes a server resource. The term "cloud computer" includes a cloud computer system which for example comprises a system of at least one cloud computer and for example a plurality of operatively interconnected cloud computers such as a server farm. Such a cloud computer is preferably connected to a wide area network such as the world wide web (WWW) and located in a so-called cloud of computers which are all connected to the world wide web. Such an infrastructure is used for "cloud computing", which describes computation, software, data access and storage services which do not require the end user to know the physical location and/or configuration of the computer delivering a specific service. For example, the term "cloud" is used in this respect as a metaphor for the Internet (world wide web). For example, the cloud provides computing infrastructure as a service (IaaS). The cloud computer can function as a virtual host for an operating system and/or data processing application which is used to execute the method of the invention. The cloud computer is for example an elastic compute cloud (EC2) as provided by Amazon Web Services™. A computer for example comprises interfaces in order to receive or output data and/or perform an analogue-to-digital conversion. The data are for example data which represent physical properties and/or which are generated from technical signals. The technical signals are for example generated by means of (technical) detection devices (such as for example devices for detecting marker devices) and/or (technical) analytical devices (such as for example devices for performing (medical) imaging methods), wherein the technical signals are for example electrical or optical signals. The technical signals for example represent the data received or outputted by the computer. The computer is preferably operatively coupled to a display device which allows information outputted by the computer to be displayed, for example to a user. One example of a display device is a virtual reality device or an augmented reality device (also referred to as virtual reality glasses or augmented reality glasses) which can be used as "goggles" for navigating. A specific example of such augmented reality glasses is Google Glass (a trademark of Google, Inc.). An augmented reality device or a virtual reality device can be used both to input information into the computer by user interaction and to display information outputted by the computer. Another example of a display device would be a standard computer monitor comprising for example a liquid crystal display operatively coupled to the computer for receiving display control data from the computer for generating signals used to display image information content on the display device. A specific embodiment of such a computer monitor is a digital lightbox. An example of such a digital lightbox is Buzz®, a product of Brainlab AG. The monitor may also be the monitor of a portable, for example handheld, device such as a smart phone or personal digital assistant or digital media player.

The invention also relates to a program which, when running on a computer, causes the computer to perform one or more or all of the method steps described herein and/or to a program storage medium on which the program is stored (in particular in a non-transitory form) and/or to a computer comprising said program storage medium and/or to a (physical, for example electrical, for example technically generated) signal wave, for example a digital signal wave, such as an electromagnetic carrier wave carrying information which represents the program, for example the aforementioned program, which for example comprises code means which are adapted to perform any or all of the method steps described herein.

Within the framework of the invention, computer program elements can be embodied by hardware and/or software (this includes firmware, resident software, micro-code, etc.). Within the framework of the invention, computer program elements can take the form of a computer program product which can be embodied by a computer-usable, for example computer-readable data storage medium comprising computer-usable, for example computer-readable program instructions, "code" or a "computer program" embodied in said data storage medium for use on or in connection with the instruction-executing system. Such a system can be a computer; a computer can be a data processing device comprising a means for executing the computer program elements and/or the program in accordance with the invention, for example a data processing device comprising a digital processor (central processing unit or CPU) which executes the computer program elements, and optionally a volatile memory (for example a random access memory or RAM) for storing data used for and/or produced by executing the computer program elements. Within the framework of the present invention, a computer-usable, for example computer-readable data storage medium can be any data storage medium which can include, store, communicate, propagate or transport the program for use on or in connection with the instruction-executing system, apparatus or device. The computer-usable, for example computer-readable data storage medium can for example be, but is not limited to, an electronic, magnetic, optical, electromagnetic, infrared or semiconductor system, apparatus or device or a medium of propagation such as for example the Internet. The computer-usable or computer-readable data storage medium could even for example be paper or another suitable medium onto which the program is printed, since the program could be electronically captured, for example by optically scanning the paper or other suitable medium, and then compiled, interpreted or otherwise processed in a suitable manner. The data storage medium is preferably a non-volatile data storage medium. The computer program product and any software and/or hardware described here form the various means for performing the functions of the invention in the example embodiments. The computer and/or data processing device can for example include a guidance information device which includes means for outputting guidance information. The guidance information can be outputted, for example to a user, visually by a visual indicating means (for example, a monitor and/or a lamp) and/or acoustically by an acoustic indicating means (for example, a loudspeaker and/or a digital speech output device) and/or tactilely by a tactile indicating means (for example, a vibrating element or a vibration element incorporated into an instrument). For the purpose of this document, a computer is a technical computer which for example comprises technical, for example tangible components, for example mechanical and/or electronic components. Any device mentioned as such in this document is a technical and for example tangible device.

Acquiring Data

The expression "acquiring data" for example encompasses (within the framework of a computer implemented method) the scenario in which the data are determined by the computer implemented method or program. Determining data for example encompasses measuring physical quantities and transforming the measured values into data, for example digital data, and/or computing (and e.g. outputting) the data by means of a computer and for example within the framework of the method in accordance with the invention. A step of "determining" as described herein for example comprises or consists of issuing a command to perform the determination described herein. For example, the step comprises or consists of issuing a command to cause a computer, for example a remote computer, for example a remote server, for example in the cloud, to perform the determination. Alternatively or additionally, a step of "determination" as described herein for example comprises or consists of receiving the data resulting from the determination described herein, for example receiving the resulting data from the remote computer, for example from that remote computer which has been caused to perform the determination. The meaning of "acquiring data" also for example encompasses the scenario in which the data are received or retrieved by (e.g. input to) the computer implemented method or program, for example from another program, a previous method step or a data storage medium, for example for further processing by the computer implemented method or program. Generation of the data to be acquired may but need not be part of the method in accordance with the invention. The expression "acquiring data" can therefore also for example mean waiting to receive data and/or receiving the data. The received data can for example be inputted via an interface. The expression "acquiring data" can also mean that the computer implemented method or program performs steps in order to (actively) receive or retrieve the data from a data source, for instance a data storage medium (such as for example a ROM, RAM, database, hard drive, etc.), or via the interface (for instance, from another computer or a network). The data acquired by the disclosed method or device, respectively, may be acquired from a database located in a data storage device which is operably to a computer for data transfer between the database and the computer, for example from the database to the computer. The computer acquires the data for use as an input for steps of determining data. The determined data can be output again to the same or another database to be stored for later use. The database or database used for implementing the disclosed method can be located on network data storage device or a network server (for example, a cloud data storage device or a cloud server) or a local data storage device (such as a mass storage device operably connected to at least one computer executing the disclosed method). The data can be made "ready for use" by performing an additional step before the acquiring step. In accordance with this additional step, the data are generated in order to be acquired. The data are for example detected or captured (for example by an analytical device). Alternatively or additionally, the data are inputted in accordance with the additional step, for instance via interfaces. The data generated can for example be inputted (for instance into the computer). In accordance with the additional step (which precedes the acquiring step), the data can also be provided by performing the additional step of storing the data in a data storage medium (such as for example a ROM, RAM, CD and/or hard drive), such that they are ready for use within the framework of the method or program in accordance with the invention. The step of "acquiring data" can therefore also involve commanding a device to obtain and/or provide the data to be acquired. In particular, the acquiring step does not involve an invasive step which would represent a substantial physical interference with the body, requiring professional medical expertise to be carried out and entailing a substantial health risk even when carried out with the required professional care and expertise. In particular, the step of acquiring data, for example determining data, does not involve a surgical step and in particular does not involve a step of treating a human or animal body using surgery or therapy. In order to distinguish the different data used by the present method, the data are denoted (i.e. referred to) as "XY data" and the like and are defined in terms of the information which they describe, which is then preferably referred to as "XY information" and the like.

BRIEF DESCRIPTION OF THE DRAWINGS

In the following, the invention is described with reference to the appended figures which give background explanations and represent specific embodiments of the invention. The scope of the invention is however not limited to the specific features disclosed in the context of the figures, wherein.

DESCRIPTION OF EMBODIMENTS

Figure 1:
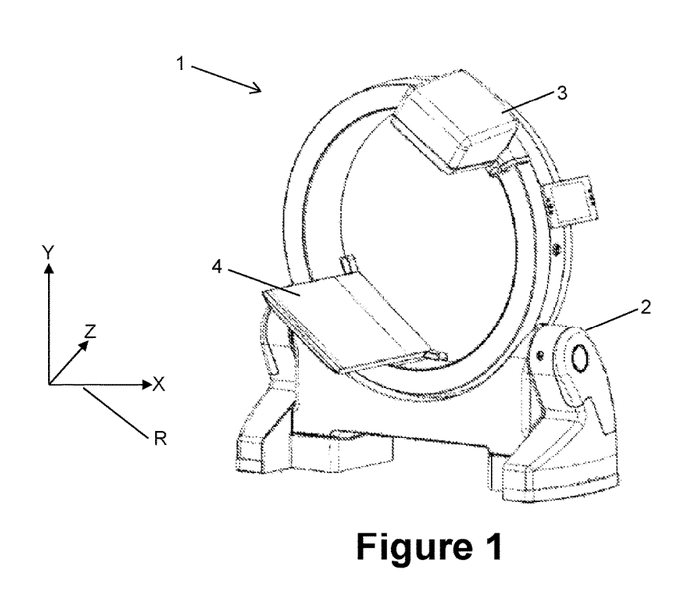
FIG. 1 illustrates a medical imaging system.

FIG. 1 schematically shows a medical imaging system 1 comprising a gantry 2 carrying an x-ray source 3 and x-ray detector 4. The gantry 2 comprises a base and a ring, wherein the ring is tiltable about at least one axis relative to the base. The base 2 comprises wheels (not shown) with which the medical imaging system 1 can be positioned, for example in an operating room.

The x-ray source 3 emits an x-ray beam which radiographs a patient (not shown) and is then detected using the detector 4 and converted into a displayable image which is recognizable by a human being.

FIG. 1 further shows a reference system R of the medical imaging system 1. The reference system R is spanned by three mutually orthogonal directions X, Y and Z and is, in the present example, virtually fixed to a room in which the medical imaging system 1 is used.

Figure 2A:
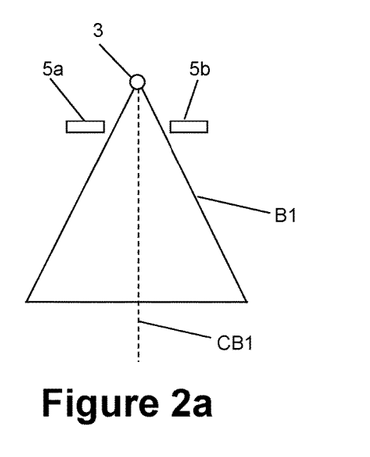
FIGS. 2a, 2b and 2c show the principles of a collimator.
Figure 2B:
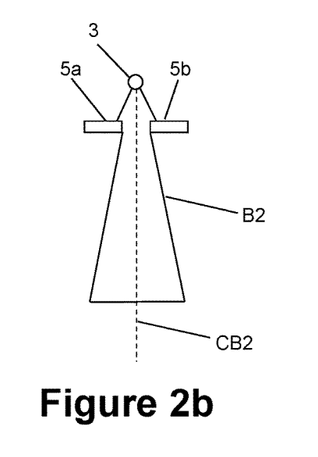
Figure 2C:
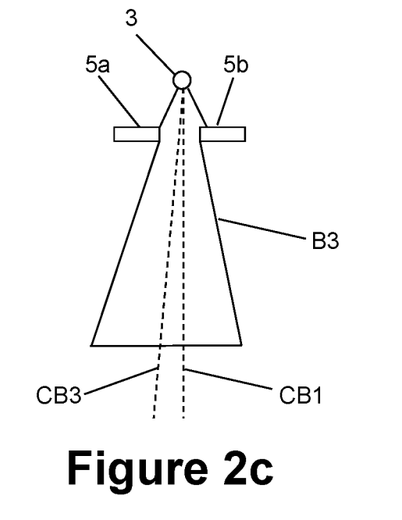

FIGS. 2a, 2b and 2c show the function of an x-ray source collimator. Shown in those figures are the x-ray source 3 which emits an original or native laser beam B1, and two collimator elements 5a and 5b of a collimator 5 (not shown in its entirety). The center of the laser beam B1 is called native central beam CB1 of the x-ray source 3. The collimator elements 5a and 5b block the incident x-ray radiation.

The collimator elements 5a and 5b can move relative to the x-ray source 3, in the present example along a line perpendicular to and intersecting with the native central beam CB1 of the x-ray source 3. FIGS. 2a, 2b and 2c are illustrative for explaining the beam shaping using the collimator 5 in one dimension. Other collimator elements are provided for collimating the x-ray beam in a second direction perpendicular to the first direction.

In the state shown in FIG. 2a, the collimator elements 5a and 5b do not interfere with the native x-ray beam B1, such that the shape and the size of the native x-ray beam B1 solely depends on the properties of the x-ray source 3.

In the state shown in FIG. 2b, the two collimator elements 5a and 5b have approached each other, thus generating a first shaped x-ray beam B2, which has a smaller opening angle than the native x-ray beam B1. Since the collimator elements 5a and 5b are arranged symmetrically to the native central beam CB1 in this state, the central beam CB2 of the first shaped x-ray beam B2 coincides with the native central beam CB1 of the native x-ray beam.

In the state shown in FIG. 2c, the collimator element 5b is closer to the native central beam CB1 than the collimator element 5a. This means that a second shaped x-ray beam B3 is shaped asymmetrically to the native center beam CB1 of the native x-ray beam B1. This means that the central beam CB3 of the second shaped x-ray beam B3 does no longer coincide with the native central beam CB1, but is tilted relative thereto. This means that the collimator 5 cannot only be used for adapting the size and/or the shape of the x-ray beam, but also for steering the direction of the x-ray beam.

Figure 3:
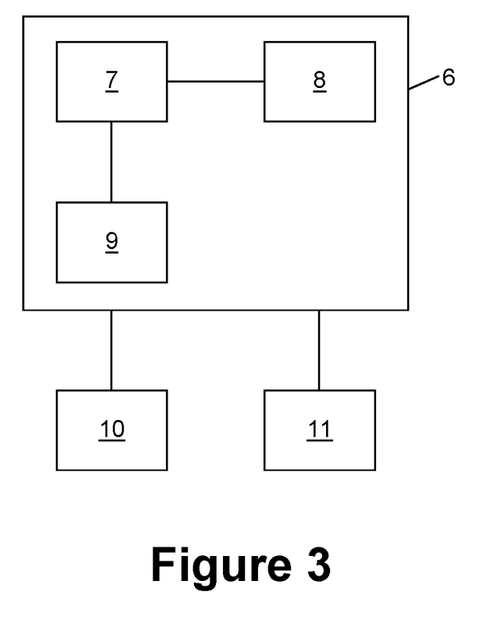
FIG. 3 is a schematic illustration of a computer for implementing the method.

FIG. 3 schematically shows a computer 6 connectable to the medical imaging system 1. The computer 6 comprises a central processing unit 7, a memory 8 and an interface 9 for connecting the computer 8 to the medical imaging system 1. The computer 8 is connected to an input device 10 such as a keyboard and/or a mouse, and an output device 11, such as a monitor. The memory 8 stores instructions which, when carried out by the central processing unit 7, implement the claimed method. The memory 8 may further store working data, such as a fluoroscopic image obtained from the medical imaging system 1. The computer 6 is further configured to control the imaging system 1 via the interface 11, for example to activate actuators (not shown) of the medical imaging system 1, for example for moving the base of the gantry 2, rotating and/or the ring of the gantry 2 or moving one or both of the x-ray source 3 and the x-ray detector 4 relative to the ring of the gantry 2.

Figure 4:
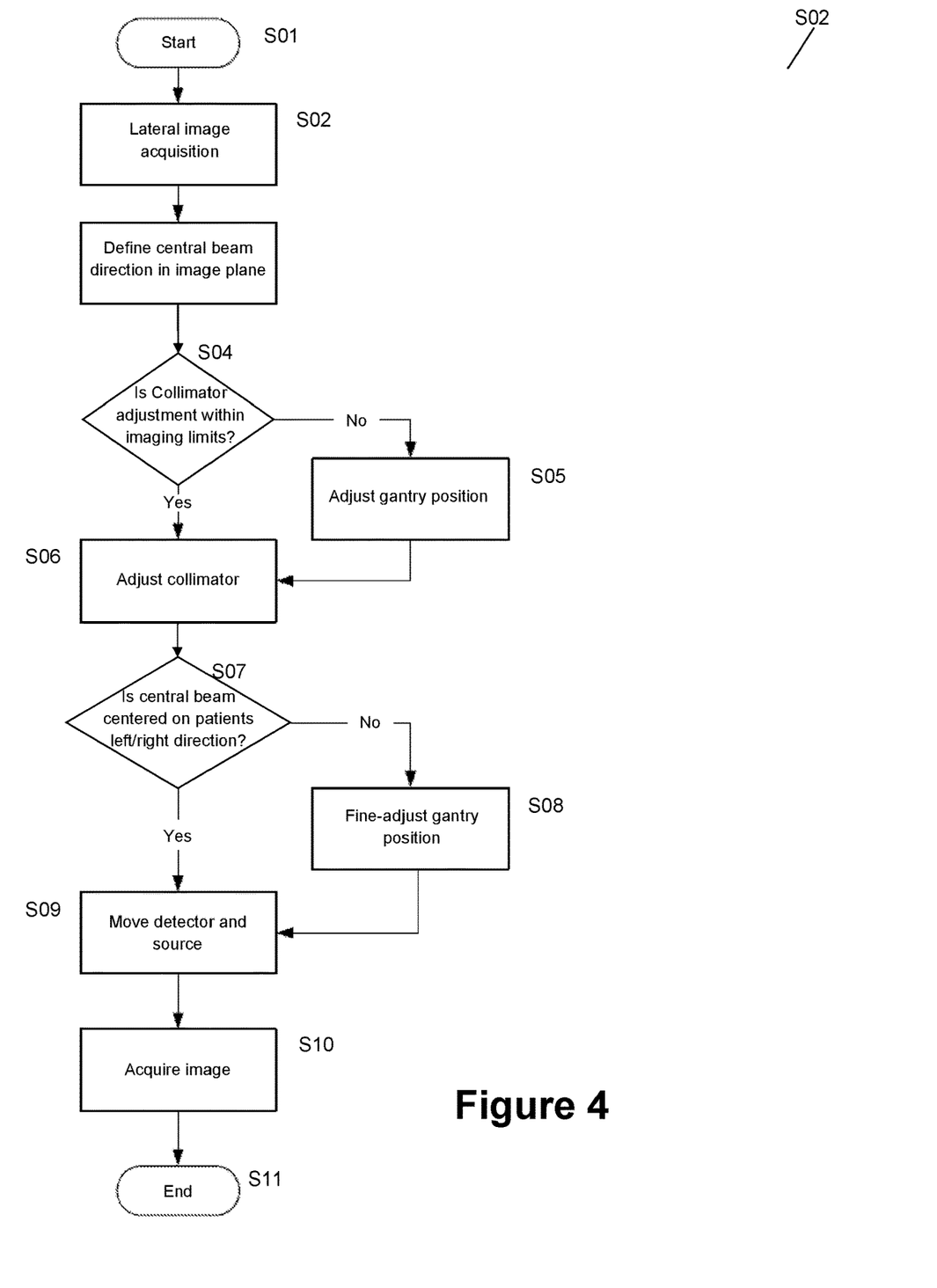
FIG. 4 shows a workflow of the method.

FIG. 4 shows an exemplary implementation of the method according to the present invention. The method starts at step S01 and acquires a lateral fluoroscopic image of at least a part of a patient in step S02. In the exemplary fluoroscopic image shown in FIG. 5, a part of the spine of the patient is imaged. The image plane of the fluoroscopic image is spanned by the X direction and the Y direction. The viewing direction of the fluoroscopic image is perpendicular to the image plane and the central beam of the medical imaging system 1 at the time of acquiring the fluoroscopic image lies in the center of the image plane. The fluoroscopic image is displayed on the output device 11.

Figure 5:
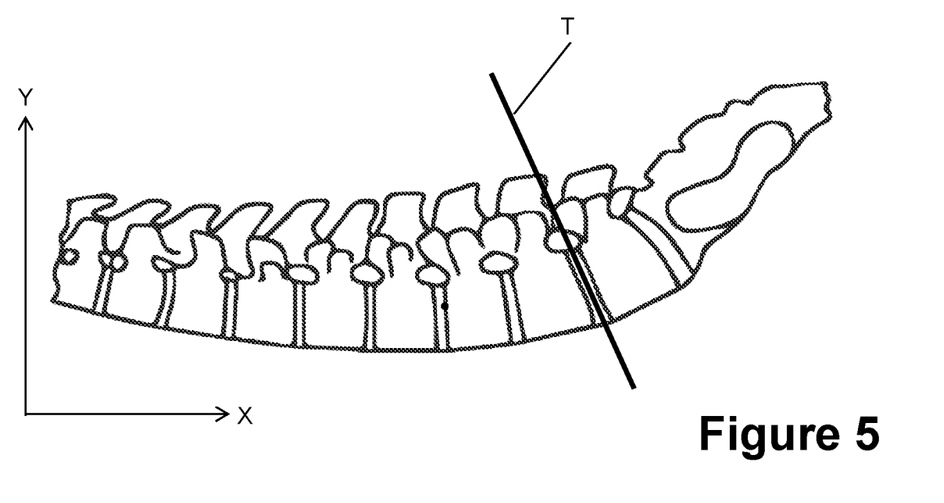
FIG. 5 shows a fluoroscopic image with a target central beam.

Step S03 involves defining a target central beam direction in the image plane. In FIG. 5, the target central beam T is drawn into the fluoroscopic image as a line by a user, for example using input device 10.

The configuration of the medical imaging system 1 upon acquisition of the lateral image is known, such that the viewing direction and the position of the central beam of the medical imaging system in the reference system R of the medical imaging system are known. This means that the target central beam T drawn into the fluoroscopic image defines a target plane in the reference system R of the medical imaging system 1.

In the present embodiment, it is assumed that the subsequent medical image is to be taken from a viewing direction which is basically the anterior-posterior direction rather than the lateral direction, but with a tilt such that the imaging direction is parallel to the end plate of a vertebra.

Step S04 then determines whether, if the rotation of the x-ray source 3 and the x-ray detector 4 about the longitudinal axis of the patient by 90 degrees was performed, the collimator adjustment is within the imaging limit. In other words, it is determined whether or not the collimator 5 can be adjusted such that the central beam of the medical imaging system 1 will coincide with the target central beam once the x-ray source 3 and the x-ray detector 4 will be rotated by 90 degrees. If this is not the case, the method proceeds to step S05, where the gantry position is adjusted. In the present embodiment, this means that the ring of the gantry 2 is tilted relative to the base of the gantry 2 such that the native central beam of the medical imaging system, after a rotation by 90 degrees, coincides with the target central beam. If required, adjusting the gantry position also involves movement of the base of the gantry 2 in a longitudinal direction of the patient to adjust the height of the central beam of the medical imaging system relative to the patient.

The method proceeds to step S06 either from step S05 or directly from step S04. In step S06, the collimator 5 is adjusted. If step S06 follows after step S05, the collimator 5 is adjusted such that the central beam of the medical imaging system 1 coincides with the native central beam of the medical imaging system and the x-ray beam shaped by the collimator 5 covers a desired region to be imaged. If step S06 follows after step S04, the collimator 5 is adjusted such that, after a rotation of the ring of the gantry 2 by 90 degrees, the central beam of the medical imaging system 1 coincides with the target central beam.

In step S07, it is determined whether the central beam would be centered on the patient's left-right direction after the rotation of the x-ray source 3 and the x-ray detector 4 by 90 degrees. If this is not the case, the method proceeds to step S08, where the gantry position is fine adjusted. In particular, the base of the gantry 2 is moved relative to the patient in a lateral direction of the patient such that the central beam will be centered on the patient's left-right direction.

This fine adjustment of the gantry position can for example be carried out using a medical navigation system which detects the position of the gantry and the position of the patient and controls a drive system of the gantry 2 or instructs an operator how to move the gantry 2 such that the central beam will be centered on the patient's left-right direction. Another option would be using a laser beam emitted by a laser (not shown) attached to the ring of the gantry 2. The laser beam for example intersects with a virtual line which is perpendicular to the plane of the ring of the gantry 2 and located in the center of the ring of the gantry 2, and is preferably parallel to the ring of the gantry 2. The laser beam then shows the orientation of the ring of the gantry 2 relative to the patient, and the position of the base of the gantry 2 can be adapted until the laser beam hits a desired position on the surface of the patient.

The method proceeds to step S09 either from step S07 or step S08. In step S09, the x-ray source 3 and the x-ray detector 4 are rotated by 90 degrees within the ring of the gantry 2 about the axis perpendicular to the ring of the gantry 2. The medical imaging system 1 is now configured to capture a subsequent medical image from the desired imaging direction drawn into the fluoroscopic image. It shall be noted that other embodiments of the medical imaging system might be designed such that the x-ray source 3 and the x-ray detector 4 do not rotate relative to the ring of the gantry 2, but together with the ring of the gantry 2 or any other carrier, such as a C-arm.

The method then proceeds to step S010 in which a subsequent medical image is acquired from the desired direction and ends at step S011.

In the example described with the reference to FIG. 4, several adjustments of the collimator and the gantry position as well as a movement of the x-ray source 3 and the x-ray detector 4 are made one after the other. However, it is also possible to first determine the required control data and then control all adjustments and rotations at the same time.

The invention claimed is:

1. A method of determining a configuration of a medical imaging system comprising an x-ray source and an x-ray detector mounted on a gantry and an x-ray source collimator for shaping the beam of the x-ray source, the configuration of the medical imaging system comprising the position of the x-ray source, the position of the x-tray detector and the settings of the x-ray source collimator, the method comprising the steps of:
   capturing a fluoroscopic image of at least a part of a patient with a known configuration of the medical imaging system,
   setting a target central beam of the medical imaging system in the fluoroscopic image,
   determining a target line in space from the target central beam and the known configuration of the medical imaging system and
   determining the configuration of the medical imaging system such that the central beam of the medical imaging system coincides with the target line in space.

2. The method of claim 1, wherein the target line in space lies in a projected plane in space defined by the position of the target central beam set in the fluoroscopic image.

3. The method of claim 2, wherein the angle between the target line in space and a reference line, which is perpendicular to the imaging plane of the x-ray detector and lies in the target plane, is within a predetermined angular range.

4. The method of claim 3, wherein the angular range from 80° to 100°.

5. The method of claim 1, further comprising the step of inputting a depth location of the target line in space in a direction perpendicular to the imaging plane of the x-ray detector.

6. The method of claim 1, further comprising the step of selecting a region of the patient to be imaged in the fluoroscopic image and determining the settings of the x-ray source collimator according to the selected region.

7. The method of claim 1, further comprising the step of selecting a region of the patient to be imaged in the fluoroscopic image and wherein determining the configuration of the medical imaging system involves the steps of:
   determining whether the x-ray source collimator is adjustable such that the central beam of the medical imaging system coincides with the target line in space and an x-ray beam shaped by the x-ray source collimator covers the region to be imaged while maintaining the current positions of the x-ray source and the x-ray detector,
   if yes, adjusting the settings of the x-ray source collimator such that the central beam of the medical imaging system coincides with the target line in space and an x-ray beam shaped by the x-ray source collimator covers the region to be unaged, and
   if not, adjusting the positions of the x-ray source and the x-ray detector such that the central beam of the medical imaging system coincides with the target line in space and determining the settings of the x-ray source collimator such that an x-ray beam shaped by the x-ray source collimator covers the region to be imaged.

8. The method of claim 7, wherein determining whether the x-ray source collimator is adjustable such that the central beam of the medical imaging system coincides with the target line in space and an x-ray beam shaped by the x-ray source collimator covers the region to be imaged while maintaining the current positions of the x-ray source and the x-ray detector involves calculating a required beam shape for imaging the selected region to be imaged and using a model of the x-ray source and the x-ray source collimator to determine whether they can form an x-ray beam of the required beam shape.

9. The method of claim 1, wherein setting the target central beam of the medical imaging system in the fluoroscopic image involves the steps of:
   automatically generating a proposed target central beam,
   overlaying the proposed target central beam over the fluoroscopic image,
   obtaining user input regarding the proposed target central bean, and modifying the proposed target central beam or approving the proposed target central beam according to the user input.

10. The method of claim 1, wherein determining the configuration of the medical imaging system such that the central beam of the medical imaging system coincides with the target line in space involves the steps of:
   acquiring a kinematic model of the medical imaging system including all degrees of freedom of the x-ray source and the x-ray detector relative to the gantry,
   determining target positions of the x-ray source and the x-ray detector in space from the target line in space and the settings of the x-ray source collimator, and
   determining the position of the gantry in space and the positions of the x-ray source and the x-ray detector relative to the gantry from the target positions of the x-ray source and the x-ray detector in space and based on inverse kinematics using the kinematic model of the medical imaging system.

11. The method of claim 1, further comprising the step of driving actuators of the medical imaging system such that the medical imaging system assumes the determined configuration.

12. A program logic stored in a memory device of a computer that when running on the computer that is connected to a medical imaging system comprising an x-ray source and an x-ray detector mounted on a gantry and an x-ray source collimator for shaping the beam of the x-ray source, causes the computer to determine the configuration of the medical imaging system, comprising the position of the x-ray source, the position of the x-ray detector and the settings of the x-ray source collimator, by executing the steps of:
   acquiring a fluoroscopic image of at least a part of a patient with a known configuration of the medical imaging system,
   setting a target central beam of the medical imaging system in the fluoroscopic image,
   determining a target line in space from the target central beam and the known configuration of the medical imaging system, and
   determining the configuration of the medical imaging system such that the central beam of the medical imaging system coincides with the target line in space.

13. A computer on which the program logic according to claim 12 is stored and/or run.

14. A system comprising the computer of claim 13 and a medical imaging system comprising an x-ray source and an x-ray detector mounted on a gantry and an x-ray source collimator for shaping the beam of the x-ray source.

15. A non-transitory computer readable storage medium storing a program that when running on a computer that is connected to a medical imaging system comprising an x-ray source and an x-ray detector mounted on a gantry and an x-ray source collimation for shaping the beam of the x-rale source, causes the computer to determine the configuration of the medical imaging system, comprising the position of the x-ray source, the position of the x-ray detector and the settings of the x-ray source collimator, by executing the steps of:
   acquiring a fluoroscopic image of at least a part of a patient with a known configuration of the medical imaging system,
   setting a target central beam of the medical imaging system in the fluoroscopic image,
   determining a target line in space from the target central beam and the known configuration of the medical imaging system, and
   determining the configuration of the medical imaging system such that the central beam of the medical imaging system coincides with the target line in space.

16. The method of claim 4, wherein the angular range is 90°.

* * * * *